United States Patent
Bleul et al.

(10) Patent No.: US 11,361,886 B2
(45) Date of Patent: Jun. 14, 2022

(54) METHOD FOR PRODUCING STABLE DISPERSIBLE MAGNETIC IRON OXIDE SINGLE-CORE NANOPARTICLES, STABLE DISPERSIBLE MAGNETIC IRON OXIDE SINGLE-CORE NANOPARTICLES AND USES OF SAME

(71) Applicant: FRAUNHOFER-GESELLSCHAFT ZUR FÖRDERUNG DER ANGEWANDTEN FORSCHUNG E.V., Munich (DE)

(72) Inventors: Regina Bleul, Wiesbaden (DE); Raphael Thiermann, Wiesbaden (DE)

(73) Assignee: Fraunhofer-Gesellschaft zurförderung der angewandten Forschung e.V., Munich (DE)

( * ) Notice: Subject to any disclaimer, the term of this patent is extended or adjusted under 35 U.S.C. 154(b) by 308 days.

(21) Appl. No.: 15/752,523

(22) PCT Filed: Aug. 5, 2016

(86) PCT No.: PCT/EP2016/068756
§ 371 (c)(1),
(2) Date: Feb. 13, 2018

(87) PCT Pub. No.: WO2017/029130
PCT Pub. Date: Feb. 23, 2017

(65) Prior Publication Data
US 2018/0240577 A1    Aug. 23, 2018

(30) Foreign Application Priority Data
Aug. 18, 2015   (DE) .................... 10 2015 215 736.9

(51) Int. Cl.
C01G 49/02    (2006.01)
C09C 1/24    (2006.01)
(Continued)

(52) U.S. Cl.
CPC ....... *H01F 1/0054* (2013.01); *A61K 49/1863* (2013.01); *C01G 49/02* (2013.01);
(Continued)

(58) Field of Classification Search
CPC .. A61K 49/1863; A61K 47/6923; C09C 1/24; C01G 49/02; C01P 2004/24; H01F 1/005
See application file for complete search history.

(56) References Cited

U.S. PATENT DOCUMENTS

| | | | |
|---|---|---|---|
| 4,376,714 A | 3/1983 | Pingaud | |
| 5,928,958 A * | 7/1999 | Pilgrimm | A61K 47/51 436/526 |

(Continued)

FOREIGN PATENT DOCUMENTS

| | | |
|---|---|---|
| CN | 1312225 A | 9/2001 |
| DE | 10 2008 015365 A1 | 9/2009 |

(Continued)

OTHER PUBLICATIONS

Girod et al., "How temperature determines formation of maghemite nanoparticles," Journal of Magnetism and Magnetic Materials 380(1): 163-167 (2015) (Available online Oct. 2014) (Year: 2014).*

(Continued)

*Primary Examiner* — Anthony J Zimmer
*Assistant Examiner* — Sean P. O'Keefe
(74) *Attorney, Agent, or Firm* — Leydig, Voit & Mayer, Ltd.

(57) ABSTRACT

The present invention relates to magnetic single-core nanoparticles, in particular stable dispersible magnetic single-core nanoparticles (e.g. single-core magnetite nanoparticles) having a diameter between 20 and 200 nm in varied morphology, and the continuous aqueous synthesis thereof, in particular using micromixers. The method is simple, quick and cost-effective to perform and is carried out without (Continued)

organic solvents. The single-core nanoparticles produced by the method form stable dispersions in aqueous media, i.e. not having a tendency to assemble or aggregate. In addition, the method offers the possibility of producing anisotropic, super-paramagnetic, plate-shaped nanoparticles which, due to their shape anisotrophy, are extremely suitable for use in polymer matrices for magnet field-controlled release of active substances.

13 Claims, 3 Drawing Sheets

(51) Int. Cl.
  *H01F 1/00* (2006.01)
  *A61K 49/18* (2006.01)
  *A61K 47/69* (2017.01)
(52) U.S. Cl.
  CPC ............... *C09C 1/24* (2013.01); *C09C 1/245* (2013.01); *A61K 47/6923* (2017.08); *C01P 2004/04* (2013.01); *C01P 2004/24* (2013.01); *C01P 2004/32* (2013.01); *C01P 2004/38* (2013.01); *C01P 2004/62* (2013.01); *C01P 2006/22* (2013.01); *C01P 2006/42* (2013.01)

(56) References Cited

U.S. PATENT DOCUMENTS

| | | | | |
|---|---|---|---|---|
| 6,423,296 | B1* | 7/2002 | Gunther | A61K 49/186 |
| | | | | 424/9.322 |
| 6,534,032 | B2 | 3/2003 | Meisen | |
| 6,638,494 | B1* | 10/2003 | Pilgrimm | A61K 9/5094 |
| | | | | 424/490 |
| 9,773,594 | B2* | 9/2017 | Carpenter | H01F 1/11 |
| 2001/0031240 | A1 | 10/2001 | Meisen | |
| 2006/0133990 | A1 | 6/2006 | Hyeon et al. | |
| 2007/0243145 | A1* | 10/2007 | Andre | A61K 8/8182 |
| | | | | 424/59 |
| 2009/0309597 | A1* | 12/2009 | Horak | A61K 49/1863 |
| | | | | 324/318 |
| 2011/0104074 | A1* | 5/2011 | Kakar | A61K 47/60 |
| | | | | 424/9.32 |
| 2012/0277517 | A1* | 11/2012 | Ivkov | A61N 1/406 |
| | | | | 600/2 |
| 2015/0320862 | A1* | 11/2015 | Ivkov | A61K 9/5015 |
| | | | | 600/12 |
| 2016/0089455 | A1* | 3/2016 | Hyeon | C08G 81/00 |
| | | | | 428/402 |

FOREIGN PATENT DOCUMENTS

| | | | | |
|---|---|---|---|---|
| DE | 102008015365 | A1* | 9/2009 | ......... A61K 49/1818 |
| GB | 2 063 233 | A | 6/1981 | |

OTHER PUBLICATIONS

Institut für Mikrotechnik Mainz GmbH, "The Catalogue, process technology of tomorrow made by imm ;/06" (2006)). (Year: 2006).*
State Intellectual Property Office of the People's Republic of China, First Office Action in Chinese Patent Application No. 201680059601.7 (dated Aug. 26, 2019).
Girod et al., "How temperature determines formation of maghemite nanoparticles," *Journal of Magnetism and Magnetic Materials* 380(1): 163-167 (2015) (Available online Oct. 2014).
Sue et al., "Continuous Hydrothermal Synthesis of $Fe_2O_3$ Nanoparticles Using a Central Collision-Type Micromixer for Rapid and Homogeneous Nucleation at 673 K and 30 MPa," *Ind. Eng. Chem. Res.* 49(18): 8841-8846 (2010).
Sue et al., "Continuous hydrothermal synthesis of $Fe_2O_3$, NiO, and CuO nanoparticles by superrapid heating using a T-type micro mixer at 673 K and 30 MPa," *Chemical Engineering Journal* 166(3): 947-953 (2011).
European Patent Office, International Search Report in International Application PCT/EP2016/068756 (dated Nov. 7, 2016).
European Patent Office, Written Opinion in International Application PCT/EP2016/068756 (dated Nov. 7, 2016).
International Bureau of WIPO, International Preliminary Report on Patentability in International Application PCT/EP2016/068756 (dated Feb. 20, 2018).
Hessel et al., "Mixing in Micro Spaces—Drivers, Principles, Designs and Uses," Chapter 1.1, *Chemical Micro Process Engineering: Processing and Plants*, 1st Edition, pp. 1-7, 272-280, 639-651, Wiley-VCH, 2005.
Lang et al., "Synthesis of Magnetite Nanoparticles for Bio- and Nanotechnology: Genetic Engineering and Biomimetics of Bacterial Magnetosomes," *Macromol. Biosci.* 7(2): 144-151 (2007).
Sugimoto et al., "Formation of Uniform Spherical Magnetite Particles by Crystallization from Ferrous Hydroxide Gels," *Journal of Colloid and Interface Science* 74: 227-243 (1980).

* cited by examiner

METHOD FOR PRODUCING STABLE DISPERSIBLE MAGNETIC IRON OXIDE SINGLE-CORE NANOPARTICLES, STABLE DISPERSIBLE MAGNETIC IRON OXIDE SINGLE-CORE NANOPARTICLES AND USES OF SAME

CROSS-REFERENCE TO RELATED APPLICATIONS

This patent application is the U.S. national phase of International Application No. PCT/EP2016/068756, filed on Aug. 5, 2016, which claims the benefit of German Patent Application No. 10 2015 215 736.9, filed Aug. 18, 2015, the disclosures of which are incorporated herein by reference in their entireties for all purposes.

The present invention relates to magnetic, single-core nanoparticles, in particular stably dispersible, magnetic, single-core nanoparticles (e.g. single-core, magnetite nanoparticles) with a diameter between 20 and 200 nm with different morphology, and the continuous, aqueous synthesis thereof, in particular with the help of micromixers. The method can be implemented easily, rapidly and economically and does not require organic solvents. The single-core nanoparticles produced by the method form stable dispersions in aqueous media, i.e. they do not have a tendency to assembling or aggregation. Furthermore, the method offers the possibility of producing anisotropic, super-paramagnetic, plate-like nanoparticles which, because of their shape anisotropy, are outstandingly suited for use in polymer matrices for magnetic field-controlled release of active substances.

At present, there is no possibility of producing economically individually stabilised, single-core iron oxide nanoparticles, the diameter of which is greater than 20 nm. However, there are various applications for which in particular nanoparticulate, magnetic, single-core iron oxides, which are greater than 20 nm in diameter, must be present individually stabilised in the dispersion medium, i.e. aggregation of the nanoparticles must not take place. These applications concern, for example, magnetic fluid hyperthermia, magnetic separation, magnetic active substance transport, magnetic active substance release, immunoassays, diagnostics applications and so-called "magnetic particle imaging".

One production method of magnetic, iron oxide nanoparticles is the standard method of co-precipitation according to the method by Massart (see DE 10 2008 015365 A1) which is used also for the industrial production of ferrofluids. However, this does not provide any single-core, iron oxide nanoparticles which have a size of at least 20 nm. Therefore, it is unsuitable for preparation of nanoparticles with a size of 20 to 200 nm.

Current production methods of magnetic, iron oxide, single-core particles with a size of at least 20 nm are based on the thermal decomposition of organic precursor molecules in high-boiling organic solvents. These methods are very energy-intensive and consume large quantities of organic solvents (see e.g. US 2006/0133990 A1). Firstly, these methods cannot be transferred easily to an industrial scale. Secondly, the nanoparticles produced in boiling organic solvents have hydrophobic properties. Consequently, transfer thereof into an aqueous medium is accompanied by the formation of nanoparticle aggregates (hydrophobic effect), which represents a problem which to date has only been solved inadequately.

It is known that iron oxide nanoparticles with a size of more than 50 nm and hydrophilic properties can be produced by the oxidation method of Sugimoto. Firstly, $Fe(OH)_2$ is hereby precipitated from an Fe(II) solution in an alkaline medium and subsequently is oxidised to magnetite by an added oxidant and temperature effects (Sugimoto & Matijevic, J. Colloid Interface Sci. 1980, 74 (1), 227-243). The particles produced in this way have, however, because of their size, already ferromagnetic properties and, in addition, have a tendency to aggregation.

In summary, it must be emphasised that neither with the method according to Massart nor with the oxidation method of Sugimoto, are there accessible individually stabilised, single-core iron oxide nanoparticles in the size between 20 and 200 nm, which have super-paramagnetic to ferromagnetic properties and a low aggregation tendency and hence are suitable also for demanding medical applications (e.g. hyperthermia or "magnetic particle imaging").

The only known possibility to date of producing stably dispersible, single-core iron oxide nanoparticles in aqueous media in this size range is a production by a biotechnological route with the help of microorganisms (Lang et al. Macromol. Biosci. 2007, 7, 144-151). The hereby produced single-core, iron oxide nanoparticles are termed magnetosomes and actually have very good physical properties (e.g. for "magnetic particle imaging"). The magnetosomes have, however, the crucial disadvantage that, because of their bacterial origin, they still include bacterial antigens and hence are strongly immunogenic. They are hence unsuitable for medical application. In addition, they have to date been able to be produced only very elaborately and in small quantities.

Starting herefrom, it was the object of the present invention to provide a method for the production of nanoparticles which are not immunogenic, have preferably super-paramagnetic properties and a comparatively high magnetic moment and do not have a tendency to aggregation formation in aqueous media.

The object is achieved by the method described herein, the features of the magnetic, single-core nanoparticles described herein, and the advantageous developments thereof. Uses of the magnetic, single-core nanoparticles according to the invention are also described.

BRIEF DESCRIPTION OF THE DRAWINGS

In FIG. 2A, plate-shaped nanoparticles (diameter approx. 30 nm, thickness approx. 3 nm) are illustrated, which were produced with the help of a short dwell loop. FIG. 2B shows spherical to cuboid nanoparticles (diameter approx. 80 nm) which were produced with the help of a long dwell loop.

DETAILED DESCRIPTION OF THE INVENTION

Figure 1:
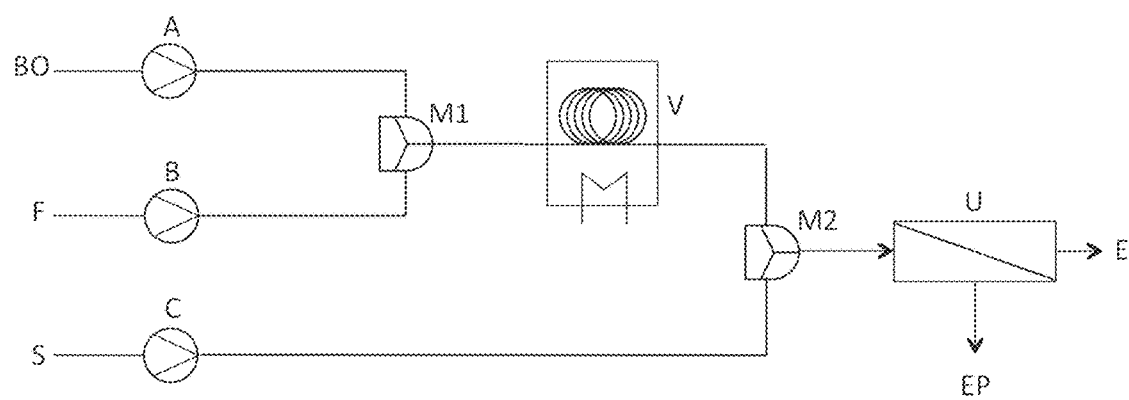
FIG. 1 shows a schematic representation of a method according to the invention.

According to the invention, a method for continuous production of stably dispersible, magnetic, single-core nanoparticles, which comprise iron oxide and stabiliser and have a diameter between 20 and 200 nm, is provided. The method comprises the steps a) preparing an aqueous solution comprising at least one base and at least one oxidant;
b) preparing an aqueous solution comprising at least one iron salt, preferably at least one Fe(II) salt, particularly preferably at least one Fe(II) salt and an iron salt which is different from an Fe(II) salt in a lower concentration than the Fe(II) salt, the concentration of Fe(II) salt to the iron salt which is different from the Fe(II) salt being in particular 4:1 or greater (optionally, no Fe(III) salt is contained in this aqueous solution);
c) preparing an aqueous solution comprising at least one hydrophilic stabiliser;
d) mixing the aqueous solution of a) and b) to form a mixture in a micromixer, $Fe(OH)_2$ being formed, which precipitates out of the solution and oxidises to form magnetic, single-core nanoparticles; and
e) mixing of the mixture from d) with the aqueous solution from c), the at least one stabiliser bonding to the iron oxide.

The method is characterised in that, in a) to e), the temperature is controlled from 10° C. to 200° C., stably dispersible, magnetic, single-core nanoparticles which comprise iron oxide and the stabiliser and have a diameter between 20 and 200 nm being produced in step e).

There are understood by nanoparticles, according to the invention, particles which can have different morphologies (e.g. spherical, ellipsoid, cuboid or disc-shaped) and have a diameter of 20 to 200 nm. There is understood by diameter, the longest three-dimensional extension of the particles (e.g. in the case of spheres the sphere diameter and in the case of discs the disc diameter). There is understood by single-core nanoparticles that the nanoparticles do not concern clusters of several nanoparticles (multicore nanoparticles) but individual nanoparticles (single-domain nanocrystals).

The central aspect of the invention is the use of a stabiliser in the production of the nanoparticles, which stabiliser can bond both to iron oxide (i.e. the iron oxide core forming during the method) and enables stabilisation thereof (formation of a homogeneous dispersion) in water. By the addition of the stabiliser in step e), a further accumulation of iron oxide on the iron oxide nanoparticles formed in step d) is inhibited, i.e. further growth of the iron oxide nanoparticles is suppressed by the stabiliser. As a result, by means of a temporal variation in the addition of the stabiliser after step d) of the method according to the invention, the size of the nanoparticles can be influenced. According to the concentration of the educts, nanoparticles can hence be prepared without difficulty in a time interval of 1 second to 24 hours, which particles have a diameter of 20 to 200 nm. It has emerged that, with suitable choice of temperature and concentrations of the starting solutions, even preparation of nanoparticles according to the invention is possible within a time frame of less than 10 minutes. In this respect, very short incubation times are possible in the method according to the invention. It was found in addition that, by means of the temporal variation (e.g. in the time period of 1 second to below 10 minutes) not only the size but also the morphology of the nanoparticles can be adjusted, shorter time intervals effecting a flat shape (plate shape) and longer time intervals a rounder shape (spherical shape or cuboid shape).

With the method according to the invention, hence also anisotropic, plate-shaped, magnetic, single-core, iron oxide nanoparticles can be produced, which particles have for example a dimension of approx. 30 nm diameter and 3 nm thickness. As a result of the plate-shape-caused anisotropy (shape anisotropy) and the super-paramagnetic properties, these single-core nanoparticles are suitable for particular applications. Under the effect of a magnetic field, the parallel magnetic field lines are orientated along the magnetic field and effect a movement force on the plate-shaped nanoparticles. If the magnetic field alternates, then the plate is moved to and fro at the frequency of the alternation. By means of this movement, it is possible, for example, to control the release of an active substance from a polymer matrix via the anisotropic, magnetic nanoparticles and/or to produce heat. As a result, the nanoparticles according to the invention are outstandingly suited to use in polymer matrices for magnetic field-controlled release of active substances and/or for hyperthermia applications.

The method according to the invention can be implemented easily and economically since the synthesis and stabilisation, including a subsequent purification, can be implemented continuously in throughflow. This allows very short synthesis times (in part a few minutes). A further advantage is that the synthesis is effected in an aqueous system, which makes the requirement for organic solvents obsolete and makes the implementation of the method more environmentally friendly. Additional method steps (e.g. precipitation and resuspension) which are necessary, for example, in the synthesis with organic solvents or in co-precipitation according to the method of Massart, are not necessary in the method according to the invention, which contributes furthermore to curtailing and simplifying the synthesis. Furthermore, a crucial advantage of the method according to the invention is that the prepared magnetic, single-core nanoparticles do not have a tendency to assembling or aggregation in aqueous media ("cluster formation"), i.e. form homogeneous stable dispersions in aqueous media.

The method according to the invention can be characterised in that, in step d), optionally also in step e), mixing takes place with a micromixer according to DIN EN ISO 10991: 2010-03. The use of a micromixer has various advantages relative to mixing in the batch process. By means of the micromixer, a continuous, reproducible production and stabilisation of the single-core nanoparticles is achieved and can be supplemented by a subsequent, possibly likewise continuously proceeding, purification (e.g. via ultrafiltration and/or diafiltration). Mixing with a magnetic agitator is not necessary, as a result of which the formation of agglomerates is avoided. Furthermore, the use of a micromixer makes possible implementation of the method in a closed system, i.e. for example a process control in the absence of air oxygen. Previously prepared, degassed, educt solutions remain hence in this degassed state.

The micromixer can comprise a multilamination micromixer, turbulent micromixer, "impinging jet" micromixer and/or "split-and-recombine" micromixer or consist thereof, the micromixer, optionally following the mixing region or mixing chamber, being characterised by an essentially non-tapering and/or essentially straight exit without abrupt change in direction and/or tapering in cross-section of the fluid flow. Particularly preferred are "caterpillar" micromixers, e.g. a micromixer with the designation "CPMM R300x12-SO" (developed by Fraunhofer ICT IMM, previously Institut für Mikrotechnik Mainz GmbH, IMM) and/or "slit interdigital" micromixers. The mentioned and also further usable micromixers are disclosed in the publication by Hessel V. et al. in Chemical Micro. Process. Engineering: Processing and Plants, Wiley 2005. The micromixers can be produced from metals or alloys, preferably stainless steel, ceramic and/or plastic materials, preferably polyetheretherketone. Polyetheretherketone has the advantage that it is very robust.

The hydrophilic stabiliser can have at least one radical which bonds to iron oxide, preferably at least two radicals which bonds to iron oxide. The radicals preferably bond via a coordinate bond to the iron oxide. The radical or radicals can be linked to a hydrophilic polymer, the radicals being selected preferably from the group consisting of phenol radical, $PO_3$ radical, histidine radical and sugar radical. Optionally, the radical or the radicals are selected from the group consisting of phenol radical, $PO_3$ radical and histidine radical. The hydrophilic polymer preferably concerns PEG or a PEG derivative. The (chemically covalent) crosslinking of PEG or a PEG derivative with a substance which has one of the above-mentioned radicals represents particularly preferred stabilisers.

The stabiliser is preferably a substance selected from the group consisting of
a) glycosidic flavonoids, preferably rutin and/or hesperidin, particularly preferably rutin hydrate;
b) phenols, preferably polyphenols, further preferably quercetin, tannin, catechol and/or lignin, particularly preferably lignin sulphonate and/or catechol-PEG;
c) phosphoric acid derivatives, preferably bisphonate, particularly preferably alendronic acid and/or derivatives hereof;
d) triphosphate, preferably pentasodium triphosphate and/or pentapotassium triphosphate;
e) polymers with more than 3 histidine radicals; and/or
f) hydrophilic polymers, preferably starch, chitosan, dextran; and/or
g) carboxylic acid or carboxylic acid anhydride, preferably polymaleic anhydride and derivatives hereof;
preferably comprises or consists of glycosidic flavonoids and/or hydrophilic polymers, particularly preferably a glycosidic flavonoid crosslinked covalently with a hydrophilic polymer, in particular rutin-PEG and/or catechol-PEG. In general, it is advantageous if the above-mentioned substance is crosslinked (chemically covalently) with PEG or a PEG derivative. In a preferred embodiment, rutin hydrate is used since it is very readily soluble even in the presence of other agents.

The aqueous solution in a), b), and/or c), preferably a) to c), is preferably prepared in demineralised and/or degassed water. The use of demineralised water has the advantage that no undesired ions have a negative effect on the iron hydroxide formation and iron oxide formation during the process. The use of degassed water has the advantage that, during the mixing in steps d) and e), oxidation effects due to air oxygen and the formation of air bubbles with undesired interface effects are prevented. During the degassing, at least 50%, preferably more than 75%, of the oxygen dissolved in equilibrium at 20° C. is removed.

In step a), b), c), d) and/or e), preferably in steps a) to e), the temperature is controlled preferably to a temperature of 10° C. to 200° C., preferably 40 to 100° C., particularly preferably 50 to 70° C., in particular 60° C. Implementation of the method in this temperature range has proved to be particularly advantageous for rapid and selective formation of iron oxide, single-core nanoparticles with a diameter of 20 to 200 nm. It was observed in addition that fine adjustment of the size of the produced nanoparticles is possible via adjustment of the temperature (e.g. in the range of 40° C. to 80° C.). The correlation was found hereby that temperature-control at higher temperatures, with otherwise identical conditions, effects a slightly larger diameter of the produced magnetic single-core nanoparticles.

Preferably, incubation takes place before and/or after addition of the stabiliser for a time period of 1 sec. to 24 h, preferably 10 sec. to 4 h, particularly preferably 30 sec. to 40 min., in particular 1 min. to 20 min. The incubation is effected in particular in a temperature-controlled dwell loop. The use of a temperature-controlled dwell loop has the advantage that, at a specific flow rate through the dwell loop, the time of exit of the solution out of the dwell loop is defined exactly. Since the mixture from step d) of the method is mixed, according to the invention, with an aqueous solution with stabiliser, the temperature-controlled dwell loop hence establishes exactly the time at which the mixture from step d) is contacted with the stabiliser and further growth of the iron oxide nanoparticles is inhibited.

A short incubation time before the addition of the stabiliser favours formation of iron oxide, single-core nanoparticles which have a plate shape, longer incubation times favour a spherical shape or cuboid shape. Most preferably, the incubation is effected before the addition of the stabiliser for a time of less than 10 minutes since it has emerged that this time suffices to produce nanoparticles in the desired size range in plate-form or spherical form or cuboid form via the method according to the invention. The short incubation time of less than 10 minutes has the effect that, via the method according to the invention, a large quantity of stably dispersible, magnetic, single-core nanoparticles with the desired sizes and morphology per unit of time can be prepared continuously. In other words, a high throughput is possible with the method according to the invention.

In a further step of the method according to the invention, the surface of the stabilised, magnetic, single-core nanoparticles can be modified, the hereby used modifier preferably comprising a substance selected from the group consisting of
a) inorganic oxides, preferably silicon oxide;
b) inorganic phosphates, preferably hydroxyapatite;
c) hard materials, preferably silicon carbide;
d) organic polymers, preferably PEG, PEG-silane, polylactide, polystyrene, polymethacrylate, polyvinyl alcohol, polyvinylpyrrolidone, polyglycolide and/or polycaprolactone; and/or
e) inorganic polymers, preferably polysiloxane;
or consisting thereof. In particular, there is understood by modification, bonding of at least one modifier to the surface of the stabilised, magnetic, single-core nanoparticles via at least one chemically covalent bond and/or via at least one non-covalent interaction (hydrogen bridge bond, dipole-dipole interaction, ionic interaction and/or hydrophobic effect). Modification of the surface (e.g. during or after step e)) extends the application possibilities of the single-core nanoparticles with a specific functionalisation of the surface and/or can also further improve the long-term stability thereof.

The concentration
a) of the base can be 10 mM to 5 M, preferably 15 mM to 1 M, particularly preferably 20 mM to 120 mM;
b) of the oxidant can be 10 mM to 5 M, preferably 15 mM to 1 M, particularly preferably 20 mM to 120 mM; and/or
c) of the Fe(II) salt can be 10 mM bis 5 M, preferably 50 mM to 500 mM, particularly preferably 100 mM to 200 mM; and/or
d) of the stabiliser can be 1 mM bis 5 M, preferably 10 mM to 1 M, particularly preferably 15 mM to 120 mM, in particular 20 mM to 50 mM.

The molar concentration ratio of
a) $Fe^{2+}$ ions to $OH^-$ ions can be 4:1 to 1:8, preferably 2:1 to 1:4;
b) $NO_3^-$ ions to $Fe^{2+}$ ions can be 20:1 to 1:4, preferably 10:1 to 1:1; and/or c) $NO_3^-$ ions to $OH^-$ ions can be 1:5 to 10:1, preferably 1:2 to 5:1.

The base can comprise an alkali hydroxide and/or ammonium hydroxide or consist thereof, preferably sodium hydroxide, potassium hydroxide, ammonium hydroxide and/or trimethylammonium hydroxide.

The oxidant can comprise a nitrate salt and/or $HNO_3$ or consist thereof, preferably an alkali nitrate and/or ammonium nitrate, particularly preferably sodium nitrate, potassium nitrate and/or ammonium nitrate. In particular, the oxidant comprises no Fe(III) ions, which supresses the proportionate formation of particles with significantly smaller particle diameters than 20 nm.

The Fe(II) salt can comprise an Fe(II) halogenide and/or Fe(II) sulphate, preferably Fe(II) chloride and/or Fe(II) sulphate, or consist thereof.

Preferably, the single-core nanoparticles are purified in a further step after step e), preferably via diafiltration and/or ultrafiltration, the single-core nanoparticles being freed in particular of salts and excess stabiliser.

Furthermore, according to the invention, magnetic, single-core nanoparticles with a diameter between 20 and 200 nm, comprising iron oxide and at least one stabiliser are provided which are producible by the method according to the invention. In contrast to single-core nanoparticles of bacterial origin, the single-core nanoparticles according to the invention have no bacterial antigens (also no traces thereof), which makes them immunotolerant. The single-core nanoparticles according to the invention have a shell-core form with an iron oxide single-core and a shell surrounding the single-core which is formed by the stabiliser and/or comprises it.

The magnetic, single-core nanoparticles can also have the shape of a plate, preferably a plate with a diameter of 20 to 200 nm and/or a thickness of 2 to 20 nm, particularly preferably with a diameter of 20 to 40 nm and/or a thickness of 2 to 10 nm, very particularly preferably with a thickness of 2 nm to 6 nm. The plate-shaped, single-core nanoparticles have a strong shape anisotropy and are super-paramagnetic. The shape anisotropy makes possible, in the alternating magnetic field, mechanical "damage" of its surroundings (matrix) and a temperature increase. In addition, plates with an identical diameter to solid spheres have a lower weight than the solid spheres, which generally improves the dispersion stability thereof.

Stably dispersed, super-paramagnetic, single-core magnetic particles are, to a particular extent, of interest for medical applications, since there, the hydrodynamic size determines for example the biodistribution. For magnetic targeting, a high magnetic moment facilitates the control of the particles in the body enormously. Also for hyperthermia applications, single-core nanoparticles in this size range are of particular interest since in general, also the specific heating rate increases with the size of the magnetic core.

As a result, the use of the magnetic, single-core nanoparticles according to the invention in medicine is proposed, preferably in a method for surgical or therapeutic treatment of the human or animal body, particularly preferably
a) for magnetic field-controlled release of an active substance;
b) for magnetic field-controlled targeting of an active substance;
c) for treatment of an illness with magnetic fluid hyperthermia; and/or
d) as contrast means or tracer in medical imaging, preferably in magnetic resonance tomography and/or "magnetic particle imaging";

in a method for surgical or therapeutic treatment of the human or animal body, the treatment concerning in particular the treatment of cancer.

Furthermore, the use of the magnetic, single-core nanoparticles according to the invention in diagnostics is proposed, preferably as sensor in diagnostics, particularly preferably as sensor in a diagnostics method which is undertaken on the human or animal body.

Furthermore, the single-core nanoparticles according to the invention find use in
a) magnetic field-controlled release of substances;
b) magnetic field-controlled separation of substances;
c) magnetic field-controlled switching of electronic components;
d) use as contrast means or tracers in imaging, preferably in magnetic resonance tomography and/or in "magnetic particle imaging";
e) production of composite materials; and/or
f) production of a ferrofluid.

It is herewith clarified that the magnetic, field-controlled uses a) to f), cited in this paragraph, do not concern uses which relate to a method for surgical or therapeutic treatment of the human or animal body.

The subject according to the invention is intended to be explained in more detail with reference to the following Figures and examples, without wishing to restrict said subject to the specific embodiments illustrated here.

FIG. 1 shows a schematic representation of a method according to the invention. A first aqueous solution BO comprising a base and an oxidant is pumped via the pump A at a speed of 7 to 10 ml/min to the first micromixer M1. There, the first aqueous solution BO impinges on the second aqueous solution F which comprises at least one Fe(II) salt and, via the pump B at a speed of 1 to 1.5 ml/min, is pumped into the micromixer M1. In the micromixer M1, the first and second aqueous solution BO, F are mixed and the mixture is pumped into a temperature-controlled dwell loop V which has an inner diameter of approx. 0.5 mm-1.6 mm and a specific, predefined length. The length of the dwell loop V establishes the incubation time before the mixture is contacted with an aqueous solution comprising stabiliser. If plate-shaped nanoparticles are to be produced, the length of the dwell loop V is short (e.g. 2 m=>short incubation duration). If spherical nanoparticles are to be produced, the length of the dwell loop V is long (e.g. 50 m=>long incubation duration). After passing through the dwell loop, the mixture is guided into the micromixer M2. There the mixture impinges on the aqueous solution S comprising at least one stabiliser which is pumped into the micromixer M2 via the pump C at a speed of 2 to 3 ml/min. In the micromixer M2, hydrophilically-stabilised, iron oxide, single-core nanoparticles according to the invention which are further purified via an ultrafiltration module U are produced. Excess educts E (salts and excess stabiliser) are hence separated from the product EP (single-core nanoparticles).

Figure 2A:
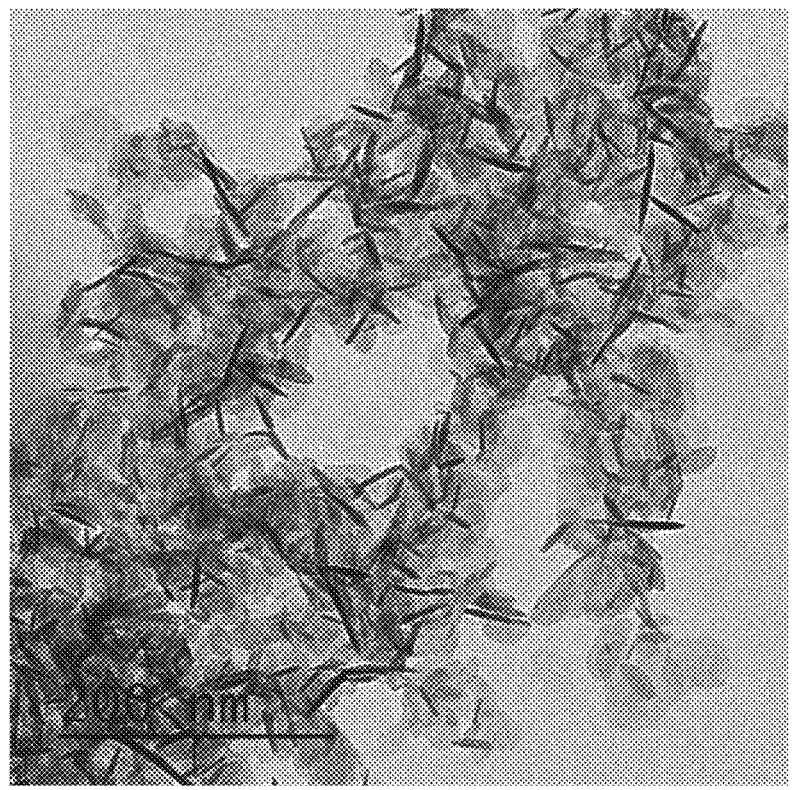
FIG. 2A-2B show a TEM picture of nanoparticles produced according to the invention.
Figure 2B:
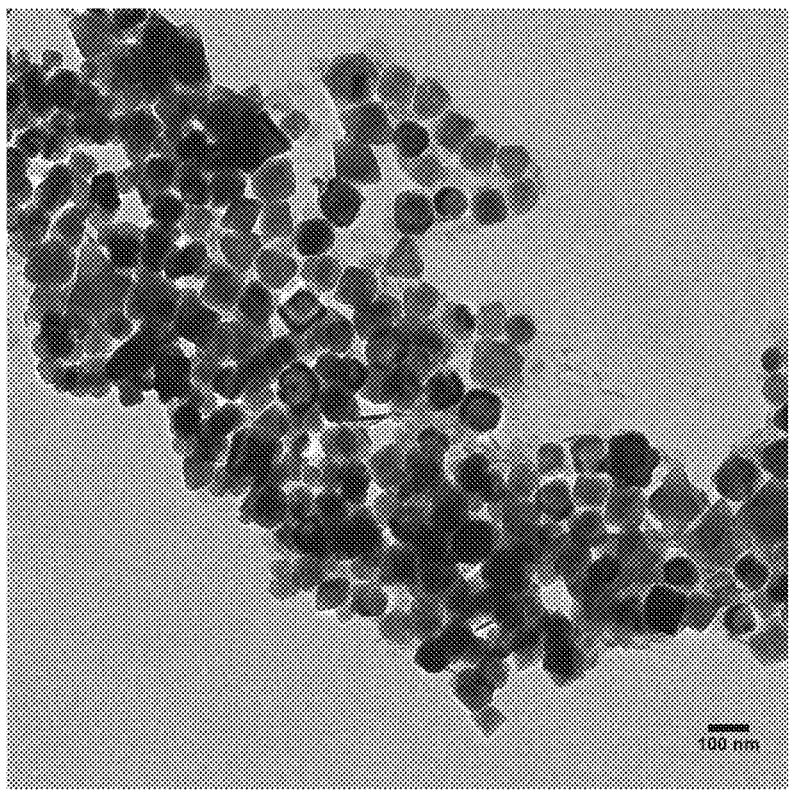

FIG. 2 shows a TEM picture of nanoparticles produced according to the invention. In FIG. 2A, plate-shaped nanoparticles (diameter approx. 30 nm, thickness approx. 3 nm) are illustrated, which were produced with the help of a short dwell loop. FIG. 2B shows spherical to cuboid nanoparticles (diameter approx. 80 nm) which were produced with the help of a long dwell loop.

Figure 3A:
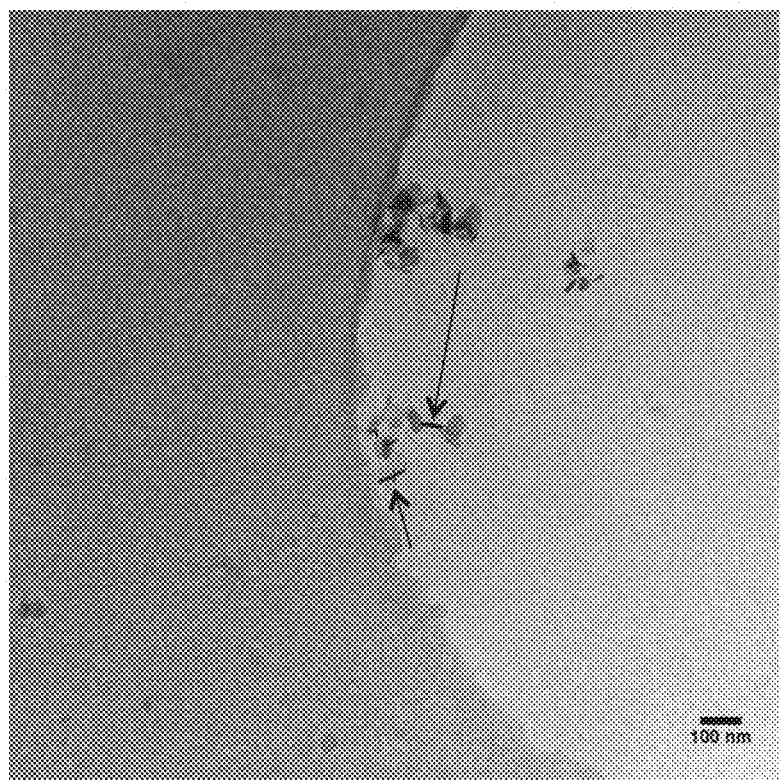
FIG. 3A-3B show a cryo-TEM picture of plate-shaped nanoparticles according to the invention. Tilting of the sample from FIG. 3B by 30° relative to the sample from FIG. 3A verifies the disc character of the nanoparticles (see the two single-core nanoparticles marked with arrows).
Figure 3B:
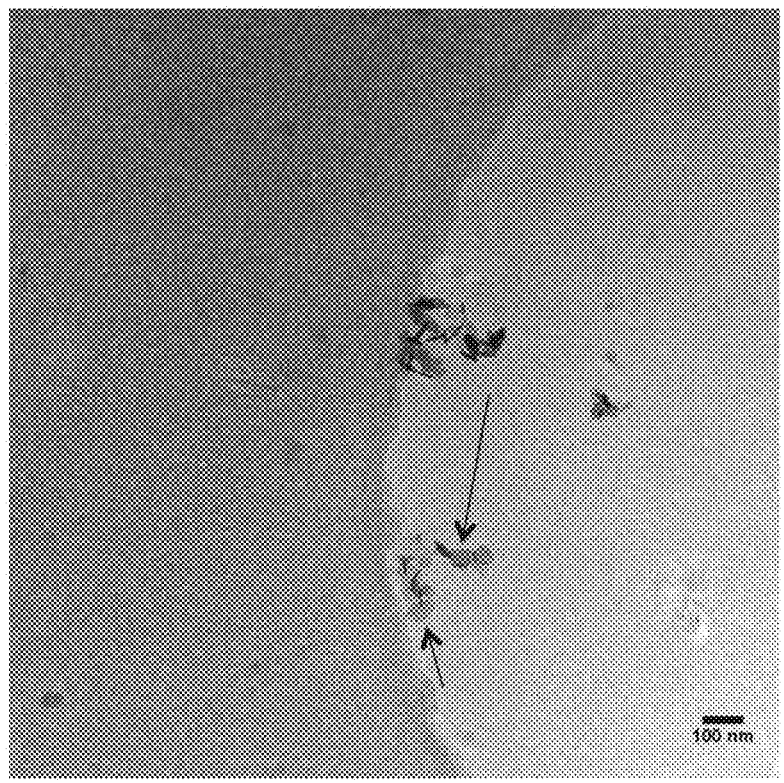

FIG. 3 shows a cryo-TEM picture of plate-shaped nanoparticles according to the invention. Tilting of the sample from FIG. 3B by 30° relative to the sample from FIG. 3A verifies the disc character of the nanoparticles (see the two single-core nanoparticles marked with arrows).

Example 1—Production of Magnetic, Iron Oxide, Single-Core Nanoparticles in Disc Form Starting solution BO: 60 mM NaOH, 54 mM $NaNO_3$ in degassed and demineralised water;
Starting solution F: 0.1 M $FeCl_2$ in degassed water;
Stabiliser solution S: 20 mM rutin hydrate in 60 mM NaOH.
All reaction solutions were preheated to 60° C., the reaction was effected at 60° C.
Pump A was operated with 10 ml/min, pump B with 1.5 ml/min and pump C with 3 ml/min. The dwell loop with inner diameter 0.5 mm was 2 m long. A micromixer was used which had the designation "CPMM R300x12-SO" made of polyetheretherketone. The disc-shaped single-core nanoparticles produced with this method are illustrated in FIG. 2A.

Particular features of these disc-shaped, magnetic particles are, in addition to the shape anisotropy, which enables magnetic switching, also the particular magnetic properties thereof, which is predestined in particular for use in (medical) imaging. Thus these particles have, for their potential application in "magnetic particle imaging", as can be proved (measurement in a magnetic particle spectrometer), comparably good signal behaviour to the samples, used at present as "gold standard" with Resovist® (Resovist® comprises ferucarbotran, i.e. a colloidal, aqueous suspension of superparamagnetic, iron oxide particles [mixture of magnetite $Fe_3O_4$ and maghemite $\gamma$-$Fe_2O_3$], which are covered with carboxydextran).

Example 2—Production of Single-Core Nanoparticles in Essentially Spherical Form or Cuboid Form Starting solution BO: 60 mM NaOH, 54 mM $NaNO_3$ in degassed water;
Starting solution F: 0.1 M $FeCl_2$ in degassed water;
Stabiliser solution S: 20 mM rutin hydrate in 60 mM NaOH.
All reaction solutions were preheated to 60° C., the reaction was effected at 60° C.
Pump A was operated with 7 ml/min, pump B with 1.05 ml/min and pump C with 2.1 ml/min. The dwell loop with inner diameter 1/16" was 50 m long in this example. A micromixer was used with the designation "CPMM R300x12-SO" made of polyetheretherketone. The cuboid single-core nanoparticles with this method are illustrated in FIG. 2B.

The invention claimed is:
1. A method for continuous production of dispersible, magnetic, single-core nanoparticles which do not assemble or aggregate in aqueous media, and which comprise iron oxide and have a diameter between 20 and 200 nm, comprising the steps of:
   a) preparing an aqueous solution comprising at least one base and at least one oxidant;
   b) preparing an aqueous solution comprising at least one iron salt and another iron salt which is different from the at least one iron salt and in a lower concentration;
   c) preparing an aqueous solution comprising at least one hydrophilic stabiliser;
   d) mixing the aqueous solution of a) and b) to form a mixture in a first micromixer, $Fe(OH)_2$ being formed, which precipitates out of the solution and oxidises to form magnetic single-core nanoparticles comprising iron oxide; and
   e) mixing the mixture from d) with the aqueous solution from c) in a second micromixer, wherein the at least one hydrophilic stabiliser bonds to the iron oxide;
   wherein, in a) to e), the temperature is controlled from 10° C. to 200° C., and
   wherein the dispersible, magnetic, single-core nanoparticles which do not assemble or aggregate in aqueous media are produced;
   wherein the hydrophilic stabiliser comprises a substance selected from the group consisting of glycosidic flavonoids, quercetin, tannin, lignin, and bisphosphonate; wherein
   the hydrophilic stabiliser has at least one residue which bonds to the iron oxide;
   the at least one residue is linked to a hydrophilic polymer; and
   the at least one residue is selected from the group consisting of a phenol residue and a sugar residue.

2. The method according to claim 1, wherein the first or the second micromixer comprises a multilamination micromixer, split-and-recombine micromixer and/or an impinging jet micromixer, the first or the second micromixer having a straight exit without tapering in cross-section of fluid flow.

3. The method according to claim 1, wherein the hydrophilic stabiliser comprises a glycosidic flavonoid crosslinked covalently with a hydrophilic polymer.

4. The method according to claim 1, wherein, in a further step, the surface of the stabilised, magnetic, single-core nanoparticles is modified to comprise a substance selected from the group consisting of:
   a) inorganic phosphates;
   b) hard materials; and
   c) PEG-silane, polylactide, polyvinylpyrrolidone, polyglycolide, or polycaprolactone, or a combination thereof.

5. The method according to claim 1, wherein the aqueous solution in at least one of a), b), and c) is prepared in demineralised and/or degassed water which has less than 50% of the oxygen compared to the oxygen which is dissolved in water at equilibrium at 20° C. and at atmospheric pressure.

6. The method according to claim 1, wherein incubation takes place before or after addition of the stabiliser for a time period of 1 sec. to 24 h in a temperature-controlled dwell loop.

7. The method according to claim 1, wherein, in a further step, the surface of the stabilised, magnetic, single-core nanoparticles is modified to comprise a substance selected from the group consisting of:
   a) inorganic oxides;
   b) inorganic phosphates;
   c) hard materials;
   d) organic polymers; and
   e) inorganic polymers.

8. The method according to claim 1, wherein the concentration is at least one of the following:
   (e) the concentration of the base in the aqueous solution prepared in step a) is 10 mM to 5 M;
   (f) the concentration of the oxidant in the aqueous solution prepared in step a) is 10 mM to 5 M;
   (g) the concentration of the at least one iron salt in the aqueous solution prepared in step a) is 10 mM to 5 M; and (h) the concentration of the stabiliser in the aqueous solution prepared in step a) is 1 mM to 5 M.

9. The method according to claim 1, wherein a molar concentration ratio in step d) is at least one of the following:
   a) a molar concentration of $Fe^{2+}$ ions to $OH^-$ ions is 4:1 to 1:8;
   b) a molar concentration of $NO_3^-$ ions to $Fe^{2+}$ ions is 20:1 to 1:4; and
   c) a molar concentration of $NO_3^-$ ions to $OH^-$ ions is 1:5 to 10:1.

10. The method according to claim 1, wherein the base comprises an alkali hydroxide and/or ammonium hydroxide.

11. The method according to claim 1, wherein the oxidant comprises a nitrate salt and/or $HNO_3$, but not Fe(III) ions.

12. The method according to claim 1, wherein the at least one iron salt comprises an Fe(II) halogenide and/or Fe(II) sulphate.

13. The method according to claim 1, wherein the single-core nanoparticles are purified in a further step after step e).

\* \* \* \* \*